US012582708B2

(12) United States Patent
Si et al.

(10) Patent No.:  US 12,582,708 B2
(45) Date of Patent:    Mar. 24, 2026

(54) RECOMBINANT INFLUENZA VIRUSES COMPRISING TRUNCATED NS1 FUSION PROTEINS

(71) Applicant: I.D.BIO., Cheongju-si (KR)

(72) Inventors: Young-Jae Si, Cheongju-si (KR);
Hyuk-Il Kwon, Cheongju-si (KR);
Yeo-Jeong Choi, Cheongju-si (KR)

(73) Assignee: I.D.BIO., Cheongju-si (KR)

( * ) Notice: Subject to any disclaimer, the term of this patent is extended or adjusted under 35 U.S.C. 154(b) by 1207 days.

(21) Appl. No.: 17/431,070

(22) PCT Filed: Feb. 10, 2020

(86) PCT No.: PCT/KR2020/001830
§ 371 (c)(1),
(2) Date: Aug. 13, 2021

(87) PCT Pub. No.: WO2020/166908
PCT Pub. Date: Aug. 20, 2020

(65) Prior Publication Data
US 2022/0133876 A1      May 5, 2022

(30) Foreign Application Priority Data
Feb. 15, 2019     (KR) ........................ 10-2019-0017556

(51) Int. Cl.
*A61K 39/145*          (2006.01)
*A61P 31/16*           (2006.01)
(Continued)

(52) U.S. Cl.
CPC ............ *A61K 39/145* (2013.01); *A61P 31/16* (2018.01); *C07K 14/005* (2013.01);
(Continued)

(58) Field of Classification Search
CPC ........ A61K 39/145; C12N 2760/16111; C12N 2760/16122
See application file for complete search history.

(56) References Cited

U.S. PATENT DOCUMENTS

2012/0251568 A1    10/2012  Garcia-Sastre et al.

FOREIGN PATENT DOCUMENTS

KR      10-2010-0102593 A      9/2010
KR          10-1492643 B1      2/2015
(Continued)

OTHER PUBLICATIONS

Luczo, J. M., et al., 2015, Molecular pathogenesis of H5 highly pathogenic avian influenza: the role of the haemagglutinin cleavage site motif, Rev. Med. Virol. 25:406-430.*
(Continued)

*Primary Examiner* — Jeffrey S Parkin
(74) *Attorney, Agent, or Firm* — Sughrue Mion, PLLC

(57) ABSTRACT

The present disclosure relates to a novel recombinant influenza virus, in which an interferon-beta gene, which is a foreign gene associated with an antiviral action, is introduced to an NS1 gene which is an influenza virus gene that is expressed first in the host to suppress the host immune system when infected with the influenza virus, and, in contrast to existing research, the interferon-beta is separated from the NS1 protein to carry out an intrinsic function of interferon-beta of inducing an antiviral action.

6 Claims, 10 Drawing Sheets
Specification includes a Sequence Listing.

ΔNS1-86 segment preparation

(51) Int. Cl.

| | | |
|---|---|---|
| *C07K 14/005* | (2006.01) | |
| *C07K 14/565* | (2006.01) | |
| *C12N 7/00* | (2006.01) | |
| *A61K 39/00* | (2006.01) | |

(52) U.S. Cl.
CPC .............. *C07K 14/565* (2013.01); *C12N 7/00* (2013.01); *A61K 2039/5254* (2013.01); *A61K 2039/5256* (2013.01)

(56) References Cited

FOREIGN PATENT DOCUMENTS

| | | | |
|---|---|---|---|
| KR | 10-2015-0104117 A | 9/2015 | |
| KR | 10-2018-0067464 A | 6/2018 | |
| KR | 1020180067464 * | 6/2018 | .............. C12N 7/00 |
| KR | 10-2018-0094145 A | 8/2018 | |
| KR | 10-2018-0096591 A | 8/2018 | |
| KR | 10-2018-0115717 A | 10/2018 | |

OTHER PUBLICATIONS

Khan, K. H., Aug. 2009, Vectors Used in Gene Manipulation—A Retrospective, Adv. Biotech J., pp. 1-8.*
Jasmina M. Luczo et al., "Molecular pathogenesis of H5 highly pathogenic avian influenza: the role of the haemagglutinin cleavage site motif", Rev. Med. Virol., 2015, pp. 406-430, vol. 25.
International Search Report of PCT/KR2020/001830 dated Mar. 16, 2021 [PCT/ISA/210].

* cited by examiner

FIG.1   △NS1-86 segment preparation
ΔNS1-86 mIFN-β
ΔNS1-86 GFP

Foreign gene expression of ΔNS1-86 mIFN-β/GFP virus in MDCK cells

FIG. 4
Growth curves of △NS1-86 mIFN-β/GFP virus in mammalian cells
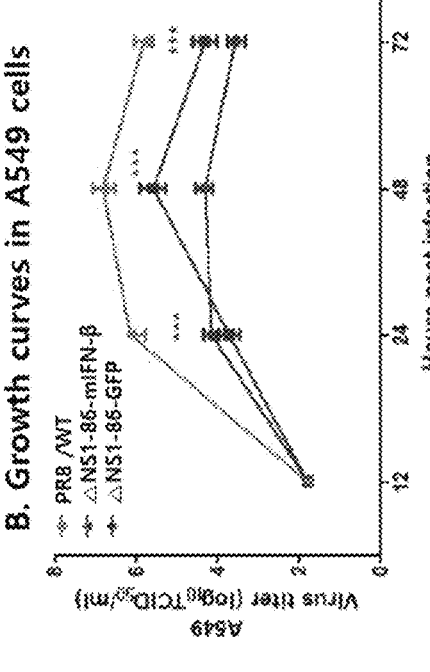
B. Growth curves in A549 cells
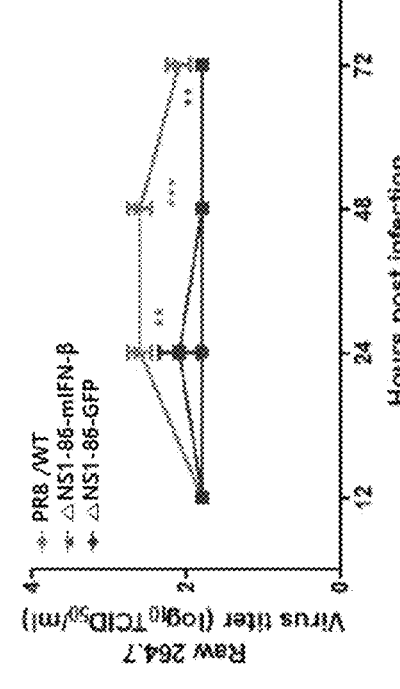
D. Growth curves in Raw 264.7 cells
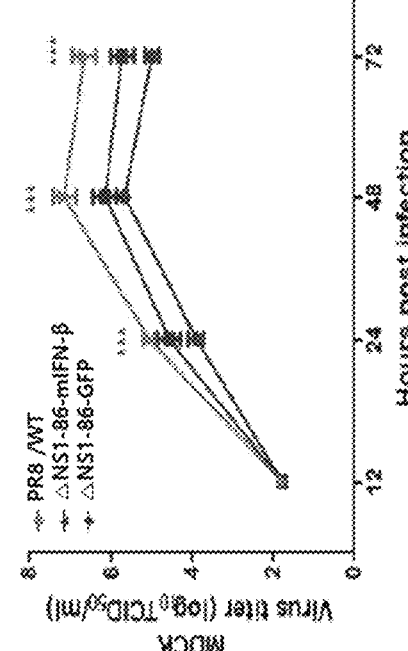
A. Growth curves in MDCK cells
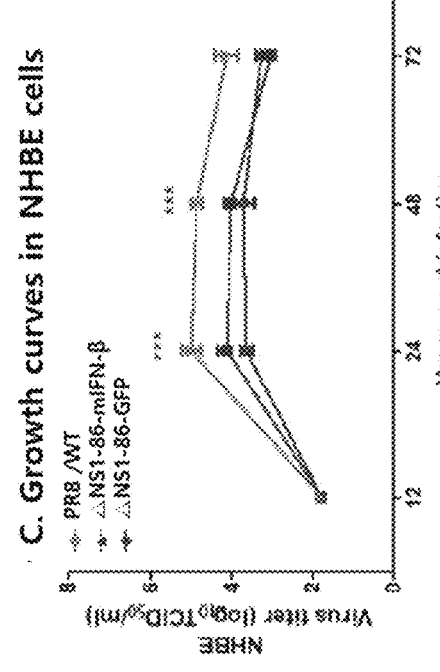
C. Growth curves in NHBE cells FIG. 5
Changes in body weight, survival rate, and virus titer in lungs after infection with △NS1-86 mIFN-β/GFP virus in BALB/c mice
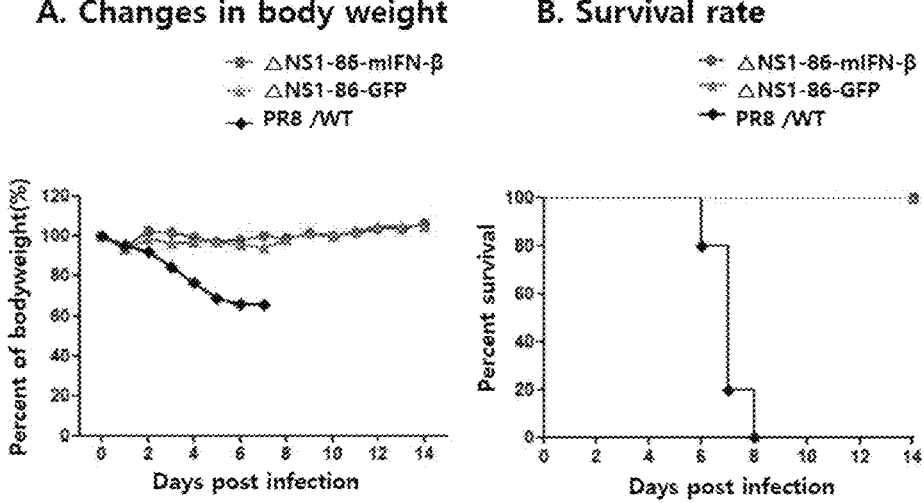
A. Changes in body weight          B. Survival rate
C. △NS1-86 mIFN-β/GFP virus titer in lungs
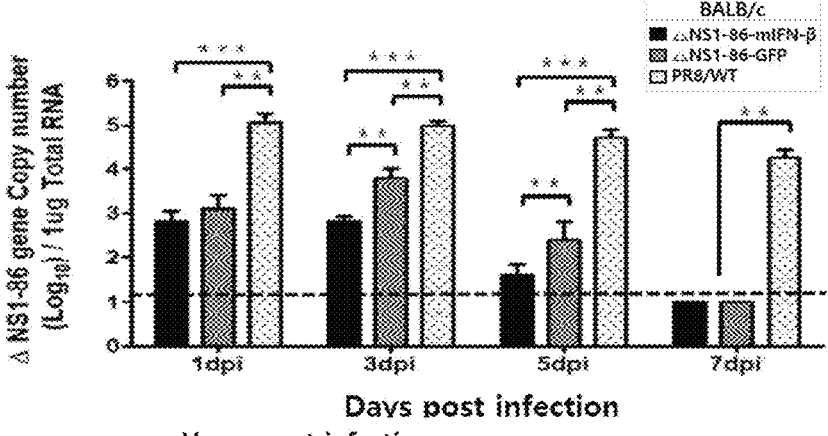

Measurement of changes in body weight, survival rate, and viral titer in lungs of mice after challenge inoculation with ma81 virus and pre-treatment with △NS1-86 mIFN-β/GFP virus in BALB/c mice

FIG. 7
Measurement of changes in body weight, survival rate, and viral titer in lungs of mice after challenge inoculation with ma81 virus and pre-treatment with △NS1-86 mIFN-β/GFP virus in B6-*Mx1⁺/⁺* mice
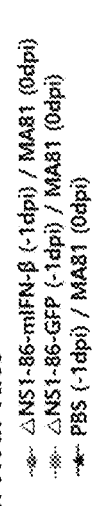
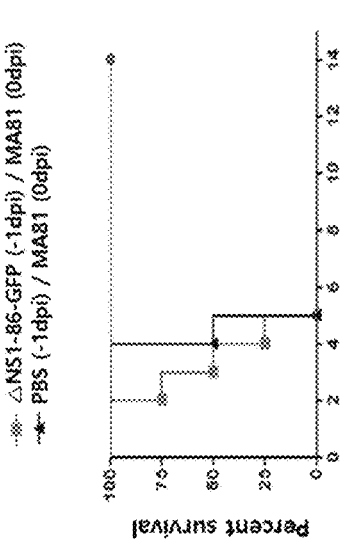
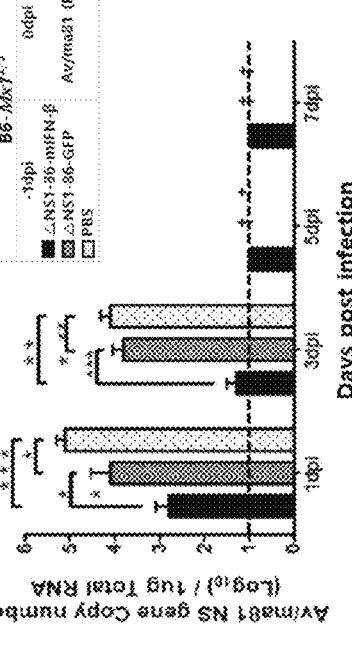
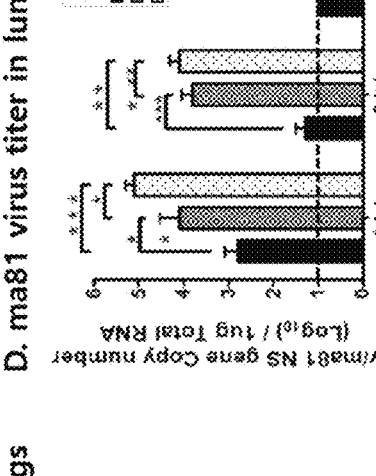
A. Changes in body weight
B. Survival rate
C. △NS1-86 mIFN-β/GFP virus titer in lungs
D. ma81 virus titer in lungs FIG. 8
Measurement of changes in body weight, survival rate, and viral titer in lungs of mice after challenge inoculation with ma81 virus and post-treatment with △NS1-86 mIFN-β/GFP virus in B6-*Mx1*⁺/⁺mice
A. Changes in body weight
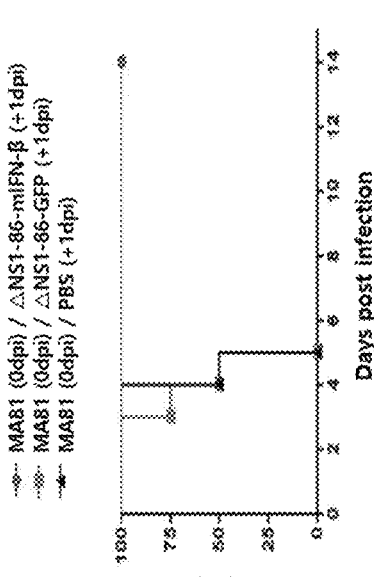
B. Survival rate
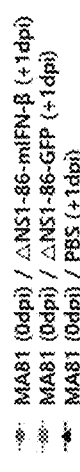
C. △NS1-86 mIFN-β/GFP virus titer in lungs
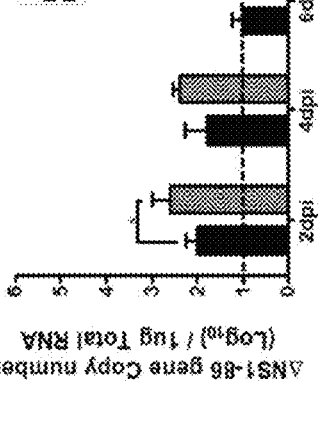
D. ma81 virus titer in lungs
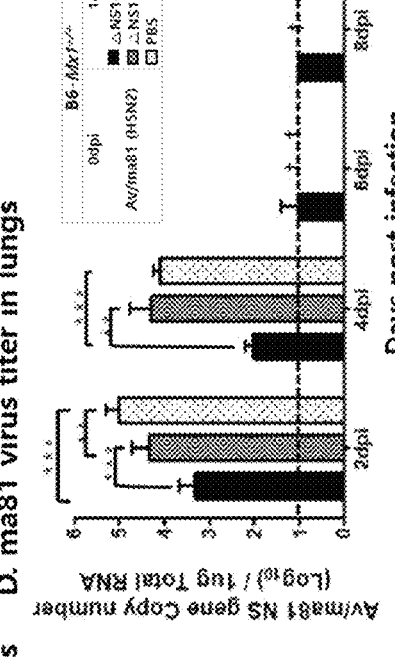

FIG. 9
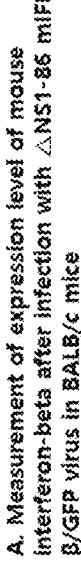
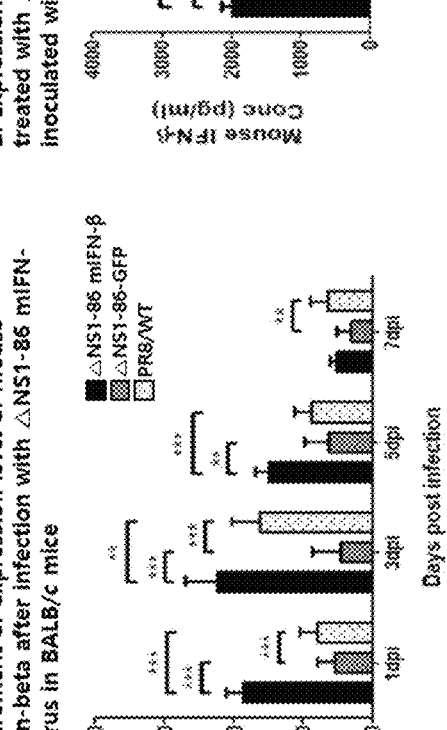
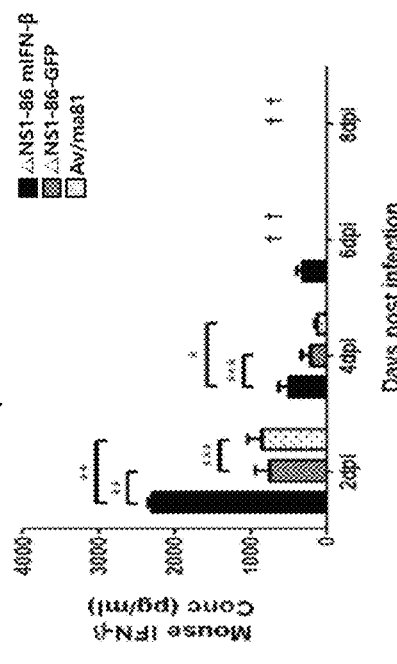

FIG. 10
Measurement of changes in body weight, survival rate, and viral titer in lungs of mice after challenge inoculation with MERS-CoV virus and post-treatment with △NS1-86 mIFN-β/GFP virus in hDPP4 mice
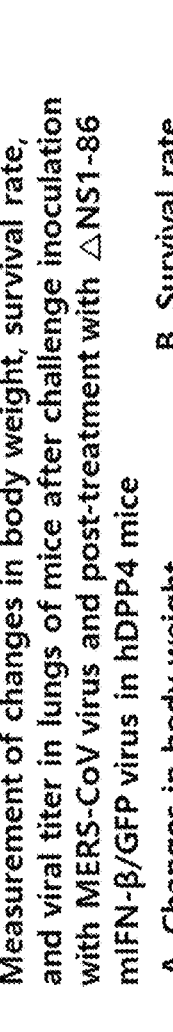
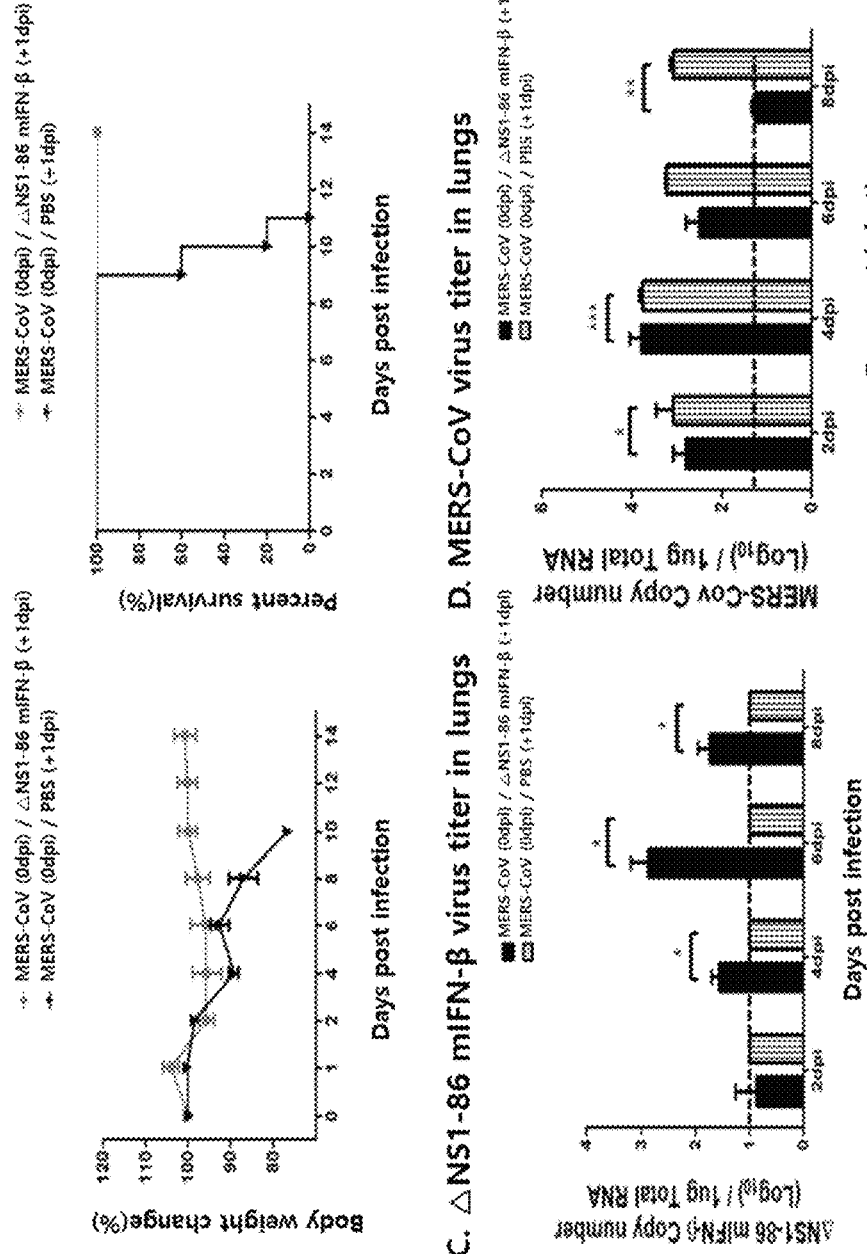

SEQUENCE LISTING

<160> NUMBER OF SEQ ID NOS: 14

<210> SEQ ID NO 1
<211> LENGTH: 258
<212> TYPE: DNA
<213> ORGANISM: Artificial Sequence
<220> FEATURE:
<223> OTHER INFORMATION: NS1-86

<400> SEQUENCE: 1

```
atggatccaa acactgtgtc aagctttcag gtagattgct ttctttggca tgtccgcaaa      60
cgagttgcag accaagaact aggtgatgcc ccattccttg atcggcttcg ccgagatcag     120
aaatccctaa gaggaagggg cagcaccctc ggtctggaca tcgagacagc cacacgtgct     180
ggaaagcaga tagtggagcg gattctgaaa gaagaatccg atgaggcact taaaatgacc     240
atggcctctg tacctgcg                                                    258
```

<210> SEQ ID NO 2
<211> LENGTH: 60
<212> TYPE: DNA
<213> ORGANISM: Artificial Sequence
<220> FEATURE:
<223> OTHER INFORMATION: Furin Cleavage site

<400> SEQUENCE: 2

```
ctcagaaata gccctcaagg agagagaaga agaaaaaaga gaggactatt tggagctata      60
```

<210> SEQ ID NO 3
<211> LENGTH: 546
<212> TYPE: DNA
<213> ORGANISM: Artificial Sequence
<220> FEATURE:
<223> OTHER INFORMATION: mouse interferon-beta

<400> SEQUENCE: 3

```
atgaacaaca ggtggatcct ccacgctgcg ttcctgctgt gcttctccac cacagccctc      60
tccatcaact ataagcagct ccagctccaa gaaaggacga acattcggaa atgtcaggag     120
ctcctggagc agctgaatgg aaagatcaac ctcacctaca gggcggactt caagatccct     180
atggagatga cggagaagat gcagaagagt tacactgcct tgccatcca agagatgctc     240 cagaatgtct ttcttgtctt cagaaacaat ttctccagca ctgggtggaa tgagactatt     300
```

-continued

```
gttgtacgtc tcctggatga actccaccag cagacagtgt ttctgaagac agtactagag     360
gaaaagcaag aggaaagatt gacgtgggag atgtcctcaa ctgctctcca cttgaagagc     420
tattactgga gggtgcaaag gtaccttaaa ctcatgaagt acaacagcta cgcctggatg     480
gtggtccgag cagagatctt caggaacttt ctcatcattc gaagacttac cagaaacttc     540
caaaac                                                                546

<210> SEQ ID NO 4
<211> LENGTH: 66
<212> TYPE: DNA
<213> ORGANISM: Artificial Sequence
<220> FEATURE:
<223> OTHER INFORMATION: porcine teschovirus-1 (PTV-1) 2A cleavage site

<400> SEQUENCE: 4
ggcagcggcg cgaccaactt tagcctgctg aaacaggcgg gcgatgtgga agaaaacccg      60
ggcccg                                                                66

<210> SEQ ID NO 5
<211> LENGTH: 366
<212> TYPE: DNA
<213> ORGANISM: Artificial Sequence
<220> FEATURE:
<223> OTHER INFORMATION: NEP

<400> SEQUENCE: 5
atggatccaa acactgtgtc aagctttcag gacatactgc tgaggatgtc aaaaatgcag      60
ttggagtcct catcgggggga cttgaatgga atgataacac agttcgagtc tctgaaactc     120
tacagagatt cgcttggaga agcagtaatg agaatgggag acctccactc actccaaaac     180
agaaacgaga aatggcggga acaattaggt cagaagtttg aagaaataag atggttgatt     240
gaagaagtga gacacaaact gaagataaca gagaatagtt ttgagcaaat aacatttatg     300
caagccttac atctattgct tgaagtggag caagagataa gaactttctc gtttcagctt     360
atttaa                                                                366

<210> SEQ ID NO 6
<211> LENGTH: 29
<212> TYPE: DNA
<213> ORGANISM: Artificial Sequence
<220> FEATURE:
<223> OTHER INFORMATION: Bm NS 1F

<400> SEQUENCE: 6
tattcgtctc agggagcaaa agcagggtg                                       29

<210> SEQ ID NO 7
<211> LENGTH: 75
<212> TYPE: DNA
<213> ORGANISM: Artificial Sequence
<220> FEATURE:
<223> OTHER INFORMATION: primer

<400> SEQUENCE: 7
tatagctcca aatagtcctc tcttttttct tcttctctct ccttgagggc tatttctgag      60
cgcaggtaca gaggc                                                      75

<210> SEQ ID NO 8
<211> LENGTH: 78
<212> TYPE: DNA
<213> ORGANISM: Artificial Sequence
```

<220> FEATURE:
<223> OTHER INFORMATION: primer

<400> SEQUENCE: 8
ctcagaaata gccctcaagg agagagaaga agaaaaaaga gaggactatt tggagctata      60
atgaacaaca ggtggatc                                                    78

<210> SEQ ID NO 9
<211> LENGTH: 84
<212> TYPE: DNA
<213> ORGANISM: Artificial Sequence
<220> FEATURE:
<223> OTHER INFORMATION: primer

<400> SEQUENCE: 9
cgggcccggg ttttcttcca catcgcccgc ctgtttcagc aggctaaagt tggtcgcgcc      60
gctgccgttt tggaagtttc tggt                                             84

<210> SEQ ID NO 10
<211> LENGTH: 84
<212> TYPE: DNA
<213> ORGANISM: Artificial Sequence
<220> FEATURE:
<223> OTHER INFORMATION: primer

<400> SEQUENCE: 10
ggcagcggcg cgaccaactt tagcctgctg aaacaggcgg gcgatgtgga agaaaacccg      60
ggcccgatgg atccaaacac tgtg                                             84

<210> SEQ ID NO 11
<211> LENGTH: 35
<212> TYPE: DNA
<213> ORGANISM: Artificial Sequence
<220> FEATURE:
<223> OTHER INFORMATION: Bm NS 890R

<400> SEQUENCE: 11
atatcgtctc gtattagtag aaacaagggt gtttt                                 35

<210> SEQ ID NO 12
<211> LENGTH: 1296
<212> TYPE: DNA
<213> ORGANISM: Artificial Sequence
<220> FEATURE:
<223> OTHER INFORMATION: recombinant NS1

<400> SEQUENCE: 12
atggatccaa acactgtgtc aagctttcag gtagattgct ttctttggca tgtccgcaaa      60
cgagttgcag accaagaact aggtgatgcc ccattccttg atcggcttcg ccgagatcag     120
aaatccctaa gaggaagggg cagcaccctc ggtctggaca tcgagacagc cacacgtgct     180
ggaaagcaga tagtggagcg gattctgaaa aagaatccg atgaggcact taaaatgacc     240
atggcctctg tacctgcgct cagaaatagc cctcaggag agagaagaag aaaaaagaga     300
ggactatttg gagctataat gaacaacagg tggatcctcc acgctgcgtt cctgctgtgc     360
ttctccacca cagccctctc catcaactat aagcagctcc agctccaaga aaggacgaac     420
attcggaaat gtcaggagct cctggagcag ctgaatggaa agatcaacct cacctacagg     480
gcggacttca agatccctat ggagatgacg gagaagatgc agaagagtta cactgccttt     540
gccatccaag agatgctcca gaatgtcttt cttgtcttca gaaacaattt ctccagcact     600

-continued

```
gggtggaatg agactattgt tgtacgtctc ctggatgaac tccaccagca gacagtgttt      660
ctgaagacag tactagagga aaagcaagag gaaagattga cgtgggagat gtcctcaact      720
gctctccact tgaagagcta ttactggagg gtgcaaaggt accttaaact catgaagtac      780
aacagctacg cctggatggt ggtccgagca gagatcttca ggaactttct catcattcga      840
agacttacca gaaacttcca aaacggcagc ggcgcgacca actttagcct gctgaaacag      900
gcgggcgatg tggaagaaaa cccgggcccg atggatccaa acactgtgtc aagctttcag      960
gacatactgc tgaggatgtc aaaaatgcag ttggagtcct catcggggga cttgaatgga     1020
atgataacac agttcgagtc tctgaaactc tacagagatt cgcttggaga agcagtaatg     1080
agaatgggag acctccactc actccaaaac agaaacgaga aatggcggga acaattaggt     1140
cagaagtttg aagaaataag atggttgatt gaagaagtga gacacaaact gaagataaca     1200
gagaatagtt ttgagcaaat aacatttatg caagccttac atctattgct tgaagtggag     1260
caagagataa gaactttctc gtttcagctt atttaa                               1296
```

<210> SEQ ID NO 13
<211> LENGTH: 7
<212> TYPE: PRT
<213> ORGANISM: Artificial Sequence
<220> FEATURE:
<223> OTHER INFORMATION: furin cleavage site

<400> SEQUENCE: 13

```
Arg Arg Arg Lys Lys Arg Gly
1               5
```

<210> SEQ ID NO 14
<211> LENGTH: 20
<212> TYPE: PRT
<213> ORGANISM: Artificial Sequence
<220> FEATURE:
<223> OTHER INFORMATION: furin cleavage site

<400> SEQUENCE: 14

```
Leu Arg Asn Thr Pro Gln Arg Glu Arg Arg Arg Lys Lys Arg Gly Leu
1               5                   10                  15

Phe Gly Ala Ile
            20
```

RECOMBINANT INFLUENZA VIRUSES COMPRISING TRUNCATED NS1 FUSION PROTEINS

CROSS REFERENCE TO RELATED APPLICATIONS

This application is a National Stage of International Application No. PCT/KR2020/001830, filed Feb. 10, 2020, claiming priority to Korean Patent Application No. 10-2019-0017556, filed Feb. 15, 2019, the entire disclosures of which are incorporated herein by reference.

TECHNICAL FIELD

The present disclosure relates to a nucleic acid in which a gene encoding a furin cleavage site and a gene encoding an NS1 protein are fused, a method for preparing the same, a recombinant vector for protein expression including the nucleic acid and a gene encoding a foreign protein, a novel recombinant influenza virus including the vector, a genetic vector including the virus, a vaccine composition including the virus, and a method for preventing or treating infection/genetic diseases with the influenza virus and its active ingredient by administering the vaccine to a subject.

BACKGROUND ART

Influenza viruses are RNA enveloped viruses with a particle size of about 125 nm in diameter. Viruses basically consist of a core of ribonucleic acid (RNA) bound to an inner nucleocapsid or nucleoprotein surrounded by a viral envelope with a lipid bilayer structure and an outer glycoprotein. The inner layer of the viral envelope consists mainly of matrix proteins, and the outer layer consists mainly of host-derived lipid materials.

The influenza virus genome is contained on 8 single RNA strands encoding 11 proteins (HA, NA, NP, M1, M2, NS1, NEP, PA, PB1, PB1-F2, PB2). The cleavage nature of the genome allows for the exchange of whole genes between different virus strains during cell cohabitation. Eight RNA cleavages contain: HA encoding hemagglutinin; NA encoding neuraminidase; NP encoding a nucleoprotein; M encoding two matrix proteins (M1 and M2) by using different detoxification mechanisms from the same RNA cleavage; NS encoding two unique nonstructural proteins (NS1 and NEP) by using different detoxification mechanisms from the same RNA cleavage; PA encoding RNA polymerase; PB1 encoding RNA polymerase and PB1-F2 protein (inducing apoptosis) by using different detoxification mechanisms from the same RNA cleavage; and PB2 encoding RNA polymerase.

These influenza viruses are highly polymorphic particles composed of two surface glycoproteins, hemagglutinin (HA) and neuraminidase (NA). Hemagglutinin mediates virus-cell membrane fusion during virus attachment to host cells and virus penetration into cells, and this surface protein, particularly hemagglutinin, is known to determine the antigenic specificity of influenza subtypes.

Influenza viruses are classified into types A, B, and C based on differences in antigens. Influenza A viruses are described by nomenclature including subtype or type, geographical origin, strain number and year of isolation, for example as A/Beijing/353/89. There are at least 16 HA subtypes (H1-H16) and 9 NA subtypes (N1-N9). All subtypes are found in birds, but H1-H3 and N1-N2 are found in humans, pigs and horses [Reference Document: Murphy and Webster, orthomyxoviruses, in Virology, ed. Fields, B. N., Knipe, D. M., Chanock, R. M., 1091-1152 (Raven Press, New York, (1990)]. Recently, in the case of HA subtypes, it has been reported that H18 and NA N11 were also found [Reference: Suxiang Tong et al, "New World Bats Harbor Diverse Influenza A Viruses" PLoS Pathogens (October 2013)].

Influenza is zoonosis, and influenza viruses are highly mutable and have the potential to spread directly from one species to another species. Hence, it is emerging as a major task to prevent the global spread of highly pathogenic influenza. In the veterinary field, the influenza virus infects almost all mammals and therefore belongs to a disease with a wide host range. In the case of industrial animals such as pigs and chickens, influenza causes enormous economic damage to farms by being a wasting disease as a single infection or mixed infection with other viruses and bacteria. Therefore, periodic vaccination is carried out through continuous live and dead vaccines.

DISCLOSURE

Technical Problem

The present inventors have tried to develop a therapeutic agent and vaccine using a gene transfer technology that can more effectively prevent and treat various infectious diseases, including influenza virus, using influenza A having various subtypes. As a result, the present inventors identified that a recombinant influenza virus prepared by introducing various foreign genes as a foreign protein gene regaion by modifying the NS1 gene having an antiviral inducing action effectively forms immune and therapeutic response against A/Ab/Korea/ma81/07/H5N2 (Av/ma81) mammalian adaptive avian influenza virus as a heterologous subtype virus, and then completed the present disclosure.

Technical Solution

One aspect of the present disclosure provides a nucleic acid in which a gene encoding a furin cleavage site consisting of the base sequence represented by SEQ ID NO: 2 and a gene encoding an NS1 protein consisting of the base sequence represented by SEQ ID NO: 12 are fused.

In addition, the present disclosure provides a recombinant vector for protein expression including a gene encoding a foreign protein and the nucleic acid.

In addition, the present disclosure provides a recombinant influenza virus including the recombinant vector for protein expression.

In addition, the present disclosure provides a genetic vector including the virus as an active ingredient.

In addition, the present disclosure provides a vaccine composition for preventing or treating influenza virus or MERS-CoV virus including the virus as an active ingredient.

In addition, the present disclosure provides a method for preventing or treating influenza virus or MERS-CoV virus infection by administering an effective amount of the vaccine to a subject.

Furthermore, the present disclosure provides a method for preparing a nucleic acid in which a gene encoding a furin cleavage site and an NS1 gene are fused, the method including: isolating the NS1 gene from an influenza virus; digesting the NS1 gene to form an NS1-86 gene; and inserting a gene encoding the furin cleavage site into the NS1-86 gene.

Advantageous Effects

The ΔNS1-86 mIFN-β/H1N1 virus of the present disclosure is effective in the treatment of immune responses and infections against A/Ab/Korea/ma81/07/H5N2 (Av/ma81) mammalian adaptive avian influenza virus as a heterologous subtype virus and MERS-CoV virus. A recombinant virus, a novel platform according to the present disclosure, has vaccine and therapeutic effects on various subtypes of influenza virus and MERS-CoV virus, and can effectively block infection of influenza virus and MERS-CoV virus, and thus can be developed as preventive and therapeutic agents for diseases.

DESCRIPTION OF DRAWINGS

FIG. 1 is a schematic diagram illustrating a process of making a ΔNS1-86 cleavage plasmid.

FIG. 4 is a graph illustrating the proliferation of ΔNS1-86 mIFN-β/GFP virus in mammalian cells.

FIG. 5 is a graph illustrating changes in body weight, survival rate, and titer in lungs of ΔNS1-86 mIFN-β/GFP virus in BALB/c mice.

FIG. 7 is a graph illustrating changes in body weight, survival rate, and viral titer in lungs of mice upon challenge inoculation with ma81 virus after pre-treatment with ΔNS1-86 mIFN-β/GFP virus in B6-Mx+/+ mice.

FIG. 8 is a graph illustrating changes in body weight, survival rate, and viral titer in lungs of mice upon post-treatment with ΔNS1-86 mIFN-β/GFP virus after challenge inoculation with ma81 virus in B6-Mx+/+ mice.

FIG. 9 is a graph illustrating the expression level of mouse interferon-beta induced by pre/post-treatment virus in mouse lungs.

FIG. 10 is a graph illustrating changes in body weight, survival rate, and viral titer in lungs of mice upon post-treatment with ΔNS1-86 mIFN-β virus after challenge inoculation with MERS-CoV in hDPP4 mice.

MODES OF THE INVENTION

Figure 2:
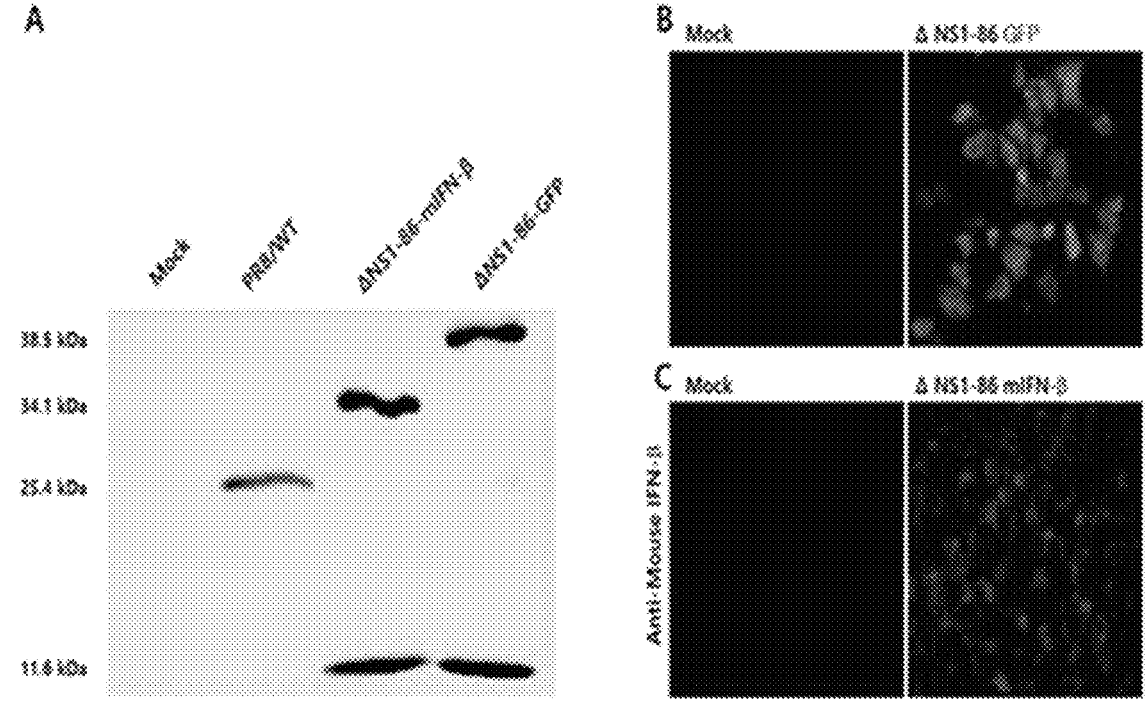
FIG. 2 illustrating an expression pattern of a foreign gene of ΔNS1-86 mIFN-β/GFP virus in MDCK cells.

Hereinafter, embodiments and examples of the present disclosure will be described in detail with reference to the accompanying drawings so that the present disclosure may be readily implemented by those skilled in the art.

However, it is to be noted that the present disclosure is not limited to the embodiments and examples but can be embodied in various other ways. In drawings, parts irrelevant to the description are omitted for the simplicity of explanation, and like reference numerals denote like parts through the entire specification.

Throughout this specification, the term "on" that is used to designate a position of one element with respect to another element includes both a case that the one element is adjacent to another element and a case that any other element exists between these two elements.

Throughout this specification, when a part is referred to as "comprising" a component, it means that it may further include other components without excluding other components unless specifically described otherwise. Terms of degree such as "about or approximately" or "substantially" used through this specification are intended to have meanings close to numerical values or ranges specified with an allowable error and intended to prevent accurate or absolute numerical values disclosed for understanding of the present disclosure from being illegally or unfairly used by any unconscionable third party. Terms of degree such as "a step of doing something" or "a step of something" used throughout this specification do not mean a step for something.

Throughout this specification, the term "combination of" included in Markush type description means mixture or combination of one or more components selected from a group consisting of components described in Markush type and thereby means that the disclosure includes one or more components selected from the group consisting of the above components.

The present disclosure relates to a nucleic acid in which a gene encoding a furin cleavage site consisting of the base sequence represented by SEQ ID NO: 2 and a gene encoding an NS1 protein consisting of the base sequence represented by SEQ ID NO: 12 are fused.

In addition, the present disclosure relates to a recombinant vector for protein expression including a gene encoding a foreign protein and the nucleic acid.

The NS1 gene is an influenza virus gene that suppresses the host immune system by first expressing in a host during influenza virus infection. The NS1 gene may be ΔNS1-86 digested after isolation from influenza virus, for example, A/PR8/1934/H1N1 virus. The NS1 gene of the A/PR8/1934/H1N1 virus is originally NS1-233, and NS1 of the wild-type virus may be digested to form the NS1 gene ΔNS1-86 (SEQ ID NO: 1) used in the present disclosure. The NS1 gene may include a polynucleotide represented by SEQ ID NO: 12, but is not limited thereto. By digesting NS1 of the wild-type virus, the wild-type virus may be attenuated, thereby inhibiting the host immune system suppression or evasion mechanism by influenza virus infection.

Genes of foreign proteins related to the antiviral action of the NS1 gene, for example, INF-β, fluorescent proteins GFP, INF-α, INF-γ, Viperin (RSAD2 (radical SAM domain-containing 2), infrared fluorescent protein (iRFP), diphtheria toxin, and glycoproteins (Gn and Gc) of the virus causing severe fever of thrombocytopenia syndrome may be inserted and fused. When the influenza virus is introduced into the body, the foreign protein is separated from the NS1 protein and performs an intrinsic antiviral induction function, thereby exhibiting an immune response against a heterologous influenza virus.

The furin cleavage site is a polybasic cleavage site known as one of the characteristics of the highly pathogenic avian influenza virus, and may be digested by a furin-like protease present in a cell or body. The foreign protein digested by furin-like protease is isolated from NS1-86 and may freely perform its intrinsic function in the body, unlike previous studies introduced to academia, and may induce antiviral action like interferon-beta of the virus according to the present disclosure.

In the conventional furin cleavage site (RRRKKR/G; SEQ ID NO: 13), the foreign gene is not cleaved when expressing the foreign gene in vivo and is expressed in a fused form with NS-86 (A of FIG. 3), whereas in the furin cleavage site according to the present disclosure (LRN-TPQRER RRKKR/G LFGAI; SEQ ID NO: 14), the NS1-86 part is properly cleaved in the fusion protein (34.1 KDa and 38.5 KDa), and a band of 11.6 kDa is identified (B of FIG. 3). Hence, it can be seen that the foreign protein is cleaved and expressed from NS-86.

Behind the foreign gene, the nuclear export protein, NEP gene, is inserted in connection with the porcine teschovirus-1 (PTV-1) 2A cleavage site, so that protein translation occurs independently of the NS1 protein in the cytoplasmic ribosome.

In addition, the present disclosure provides a recombinant influenza virus including the recombinant vector for protein expression and a genetic vector including the virus.

In addition, the present disclosure provides a vaccine composition that induces an immune response against influenza virus or MERS-CoV virus, which may infect and cause diseases in susceptible host animals. Preferably, the vaccine of the present disclosure may include a recombinant influenza virus including the recombinant vector for protein expression as an active ingredient.

The recombinant influenza virus may exhibit an immune response against A/Ab/Korea/ma81/07/H5N2 (Av/ma81) mammalian adaptive avian influenza virus or MERS-CoV virus, but is not limited thereto.

The host animal to which the vaccine of the present disclosure may exhibit an immune response may be a mammal or bird, and may include, for example, humans, dogs, cats, pigs, horses, chickens, ducks, turkeys, ferrets, and the like.

The vaccine of the present disclosure may be an attenuated live vaccine. As used herein, the term "live vaccine" refers to a vaccine including a live viral active ingredient. The term "attenuation", as used herein, is intended to mean artificial reduction in the toxicity of living pathogens, and mean inducing immunity by stimulating only the immune system without causing diseases in the body by mutating a gene involved in the essential metabolism of the pathogen. Generally, attenuation of the virus may be achieved through UV radiation, chemical treatment, or in vitro sequential high-order subculture. An explicit genetic alteration, such as the deletion of a specific nucleotide in a viral sequence known to provide toxicity or the insertion and the mutation of a nucleotide into a viral genome, may also result in attenuation.

The vaccine of the present disclosure may further include at least one selected from the group consisting of a solvent, an immunity enhancer (adjuvant) and an excipient. The solvent may include physiological saline or distilled water, and the immunity enhancer may include Freund's incomplete or complete adjuvant, aluminum hydroxide gel, and vegetable and mineral oil. Further, the excipient may include, but is not limited to, aluminum phosphate, aluminum hydroxide or aluminum potassium sulfate. It may further include materials used in preparing vaccines well known to those skilled in the pertinent field.

The vaccine of the present disclosure may include the recombinant influenza virus in an amount of $2^3$ to $2^8$ HAU (hemagglutination unit), but is not limited thereto. When the hemagglutination unit of the vaccine is less than $2^2$ HAU, it may not be able to effectively induce antibody formation in a target subject for administration. When the hemagglutination unit of the vaccine exceeds $2^8$ HAU, it may be uneconomical compared to efficiency.

The vaccine of the present disclosure may be prepared as an oral or parenteral formulation, preferably an injection solution, which is a parenteral formulation, and may be administered via intradermal, intramuscular, intraperitoneal, nasal or epidural routes.

In addition, the recombinant influenza virus of the present disclosure may be prepared by isolating the NS1 gene from an influenza virus; digesting the NS1 gene to form an NS1-86 gene; and inserting a gene encoding the furin cleavage site into the NS1-86 gene.

The influenza virus may be an influenza A virus, for example, A/PR8/1934/H1N1 virus.

The recombinant influenza virus may be prepared, for example, by the process illustrated in FIG. 1. FIG. 1 illustrates the general structure of the NS gene of the influenza A virus and the preparation process of the recombinant NS1 gene ΔNS1-86 cleavage. The preparation process of the ΔNS1-86 cleavage may be largely divided into steps 1 and 2. Step 1 is a process of inducing the ΔNS1-86 cleavage in the NS gene of the wild-type virus A/PR8/1934/H1N1 virus. The NS1 gene of the A/PR8/1934/H1N1 virus is originally NS1-233, whereas the NS1 of the virus used in the present disclosure is ΔNS1-86. By digesting NS1 of the wild-type virus, the wild-type virus may be attenuated, thereby inhibiting the host immune system suppression or evasion mechanism by influenza virus infection. Accordingly, digested NS1-86 was prepared using PCR technique, and a foreign gene, mouse interferon-beta, or a fluorescent protein, GFP, was inserted into ΔNS1-86. When a foreign gene was inserted, a furin cleavage site (LRNTPQRERRRKKR/GLF-GAI; SEQ ID NO: 14), a polybasic cleavage site known as one of the characteristics of the highly pathogenic avian influenza virus, was inserted between ΔNS1-86 and a foreign gene, and was prepared to be digested by a furin-like protease present in a cell or body. The foreign protein digested by furin-like protease is isolated from NS1-86 and may freely perform its intrinsic function in the body, unlike previous studies introduced to academia, and may induce antiviral action like interferon-beta of the virus according to the present disclosure. In addition, behind the foreign gene, the nuclear export protein, NEP gene, is inserted in connection with the porcine teschovirus-1 (PTV-1) 2A cleavage site, and thus is prepared based on the PCR technique so that protein translation may occur independently of the NS1 protein in the cytoplasmic ribosome.

In step 2, the NS1-86, foreign gene, and NEP prepared in step 1 are prepared as a single cleavage using the fusion PCR technique, and the prepared ΔNS1-86 mouse interferon-beta (mIFN-β)/GFP cleavage is transfected into 293t cells using a reverse genetics technique together with PR8 backbone to prepare ΔNS1-86 mIFN-β/GFP virus.

The present disclosure also relates to a method for preventing or treating influenza virus or MERS-CoV virus infection diseases by administering an effective amount of the vaccine to a subject suspected of influenza virus infection.

In the present disclosure, the term "influenza virus infection disease" refers to a disease caused by influenza virus infection, and may include sinusitis, paroxysmal asthma, otitis media, cystic fibrosis, bronchitis, pneumonia, and diarrhea (Pitkaranta and Hayden, 1998. Ann. Med.), however, the present disclosure is not limited thereto.

In the present disclosure, the term "subject" refers to all animals including humans that have already been infected with or may be infected with the influenza virus, and the disease may be effectively prevented and treated by administering a composition including the extract of the present disclosure to a subject. For example, the composition of the present disclosure may treat humans infected with influenza virus or MERS-CoV virus of a variety of influenza virus subtypes or variants. In addition, the composition of the present disclosure may treat chickens or pigs infected with avian influenza virus of a variety of influenza virus subtypes or variants. The composition of the present disclosure may be administered in combination with the existing therapeutic agent for influenza virus or MERS-CoV virus infection diseases.

In the present disclosure, the term "prevention" means all actions for inhibiting influenza virus infection or delaying influenza outbreak through the administration of the composition. In the present disclosure, the term "treatment" means all actions by which symptoms resulting from influenza virus infection are relieved or take a turn for the better through the administration of the composition.

In a pharmaceutically effective amount, the composition according to the present disclosure is administered. The term "pharmaceutically effective amount" is intended to refer to an amount that is sufficient to treat a disease with a reasonable benefit/risk ratio applicable to medical treatment. The effective dose level may be determined depending on the type and severity of a subject, age, gender, type of virus infected, drug activity, sensitivity to drugs, administration time, route of administration, excretion rates, duration of treatment, factors including concomitant drugs, and other factors well known in the medical field. The composition of the present disclosure may be administered as a single therapeutic agent or in combination with other therapeutic agents, and may be administered sequentially or simultaneously with conventional therapeutic agents. The composition may be administered in a single dosage or multiple dosages. Taking all of the above factors into consideration, it is important to administer an amount that may obtain the maximum effect with a minimum amount without side effects, and may be easily determined by those skilled in the art.

The advantages and features of the present disclosure and methods of achieving them will be apparent from the examples that will be described in detail. Hereinafter, the present disclosure will be described in detail by way of examples. However, these examples are for describing the present disclosure in detail, and the scope of the present disclosure is not limited to these examples.

Preparation Example 1

Preparation of Recombinant Influenza Virus Including NS1 Gene Fused with Foreign Protein Gene of Present Disclosure The present inventors fused a foreign protein with an NS1 gene of (A/PR/8/1934 (H1N1)) influenza virus to induce independent expression of the foreign protein simultaneously with influenza virus infection. In order to develop an influenza virus vaccine and therapeutic agent having a preventive and therapeutic effect upon infection of an influenza virus having a recombinant NS1 gene, first, the NS1 (non-structural protein) and NEP (nuclear export protein) were isolated from the NS gene of (A/PR/8/1934 (H1N1)) virus, then, the NS1 gene and the foreign protein were fused, and then the NS1-foreign protein portion and the NEP portion were fused to prepare a recombinant NS gene and were included in the backbone virus (A/PR/8/1934 (H1N1)) of the current human vaccine to prepare a recombinant virus.

First, to prepare a recombinant NS1 gene, the NS1-86 region (SEQ ID NO: 1) of (A/PR/8/1934 (H1N1)); and a polybasic cleavage site, a furin cleavage site (SEQ ID NO: 2) (amino acid sequence: LRNTPQRERRRKKR/GLFGAI) were fused, and then a mouse interferon-beta region (SEQ ID NO: 3) was fused. Then, the porcine teschovirus-1 (PTV-1) 2A cleavage site (SEQ ID NO: 4) was inserted into the mouse interferon-beta region, and the NEP region (SEQ ID NO: 5) of (A/PR/8/1934 (H1N1)) was fused to prepare one recombinant NS gene (SEQ ID NO: 12).

Specifically, A/PR/8/1934 (H1N1) constructed the NS1-86 domain region (SEQ ID NOs: 1 and 2) of A/PR/8/1934 (H1N1) using a primer (5-TAT AGC TCC AAA TAG TCC TCT CTT TTT TCT TCT TCT CTC TCC TTG AGG GCT ATT TCT GAG CGC AGG TAC AGA GGC-3; SEQ ID NO: 7) specifically recognizing Bm NS IF (5-TAT TCG TCT CAG GGA GCA AAA GCA GGG TG-3; SEQ ID NO: 6) and NS1-86 and a polybasic cleavage site, the furin cleavage site. A primer (5-CTC AGA AAT AGC CCT CAA GGA GAG AGA AGA AGA AAA AAG AGA GGA CTA TTT GGA GCT ATA ATG AAC AAC AGG TGG ATC-3; SEQ ID NO: 8) that specifically recognizes the mouse interferon-beta domain region (SEQ ID NO: 3) and a primer (5-CGGGCCCGGGTTTTCTTCCA-CATCGCCCGCCTGTTTCAGCAGGCTAAAGT TGGTCGCGCCGCTGCCGTTTTGGAAGTTTCTGGT-3; SEQ ID NO: 9) that specifically recognizes the porcine teschovirus-1 (PTV-1) 2A cleavage site were used to construct the mouse interferon-beta domain region (SEQ ID NOs: 3 and 4), and a primer (5-GGC AGC GGC GCG ACC AAC TTT AGC CTG CTG AAA CAG GCG GGC GAT GTG GAA GAA AAC CCG GGC CCG ATG GAT CCA AAC ACT GTG-3; SEQ ID NO: 10) that specifically recognizes the NEP domain (SEQ ID NO: 5) and Bm NS 890R (5-ATA TCG TCT CGT ATT AGT AGA AAC AAG GGT GTT TT-3; SEQ ID NO: 11) were used to construct the NEP domain region to construct each gene fragment. Bm NS IF (SEQ ID NO: 6) and Bm NS 890R (SEQ ID NO: 11) were used to prepare a recombinant NS gene (SEQ ID NO: 12) of the present disclosure through fusion and amplification through a fusion PCR process.

The recombinant NS gene of the present disclosure prepared as above was inserted into the expression vector vPHW2000 (Thesis used: J Gen Virol. 2013 June; 94(Pt 6):1230-5.doi: 10.1099/vir.0.051284-0. Epub 2013 Mar. 13.) and prepared. The expression vector into which the genes of SEQ ID NO: 1 (NS1-86), SEQ ID NO: 2 (a furin cleavage site, which is a polybasic cleavage site), SEQ ID NO: 3 (mouse interferon-beta), and SEQ ID NO: 4 (NEP) are inserted, was all mixed using TransIT-LT1 transfection reagent (Minis Bio), and then was left at room temperature for 40 minutes. The vector mixture was carefully added to the 293t cells (ATCCCCL-81™) prepared 24 hours ago, and then the culture medium was replaced with a serum-free culture medium (GIBCO™ Opti-MEM I Reduced-Serum Medium (1×) liquid) after 6 hours. 36 hours after transfection, 1 ml of Opti-MEM I containing 0.2 μg/ml of L-1-tosylamido-2-phenylehtyl chlorometyl ketone (TPCK)-trypsin (Sigma-Aldrich) was added to the transfected cells. After 48 hours, the supernatant was infected using MDCK cells, and after 48 hours, the recombinant virus of the present disclosure was isolated from the MDCK cells. The isolated recombinant virus was named ΔNS1-86 mIFN-β, and was used in the present experiment.

Example 1

24 hours after infecting MDCK cells with the ΔNS1-86 mIFN-β/GFP virus prepared as in Preparation Example 1 at an MOI of 0.001, it was identified whether the foreign protein gene of the ΔNS1-86 mIFN-β/GFP virus was expressed in MDCK cells. A of FIG. 2 shows the western blot results, and it can be indirectly seen that ΔNS1-86 was digested from ΔNS1-86 mIFN-βto independently express foreign genes. In B and C of FIG. 2, it can be seen that foreign genes were directly expressed by observing GFP and mIFN-βfluorescence expression through a fluorescence microscope 24 hours after MDCK cells were infected with ΔNS1-86 mIFN-β/GFP virus at an MOI of 0.0001 (p<0.0001).

In addition, after infecting MDCK cells with the ΔNS1-86 mIFN-β/GFP virus prepared in the same manner as in Preparation Example 1 at an MOI of 0.001, except that a conventional cleavage site (RRRKKR/G) was inserted instead of the furin cleavage site, after 24 hours, it was identified whether the foreign protein gene of the ΔNS1-86 mIFN-β/GFP virus was expressed in MDCK cells, and was compared with the ΔNS1-86 mIFN-β/GFP virus of Preparation Example 1 into which a furin cleavage site was inserted. IFN-B or GFP alone could not be detected with the antibodies available so far, so in this experiment, it was identified only with the NS-1 monoclonal antibody. Expression of IFN-B and GFP was identified through the previously presented ELISA (IFN-B) and IFA (GFP).

Figure 3:
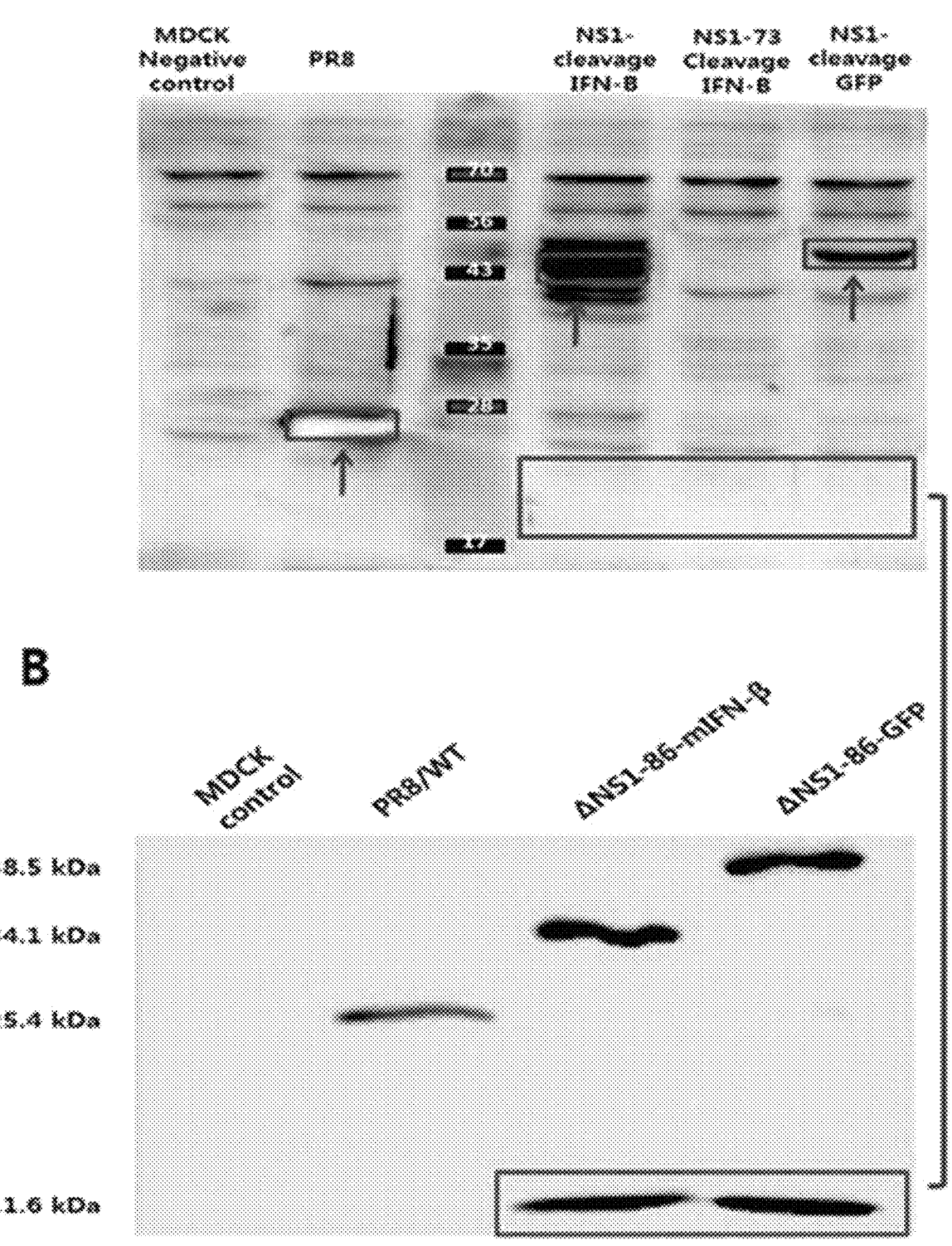
FIG. 3 illustrates an expression pattern of a foreign gene of ΔNS1-86 mIFN-β/GFP virus in MDCK cells according to the insertion of a furin cleavage site sequence.

As can be seen in A of FIG. 3, digesting of the foreign protein from NS1-86 did not occur with the conventional furin cleavage site (RRRKKR/G; SEQ ID NO: 13), so the NS1-86 (11.6 kDa) band was not detected (blue box in A of FIG. 3). Therefore, it was identified that IFN-β and GFP cleavage did not occur when a general cleavage site was inserted. Unlike this, when the furin cleavage site (LRN-TPQRER RRKKR/G LFGAI SEQ ID NO: 14) according to the present disclosure was inserted, the NS1-86 portion was digested from the fusion protein (34.1 KDa and 38.5 KDa), so that the NS1-86 (11.6 kDa) band was detected (blue box in B of FIG. 3). Hence, it can be seen that the cleavage of IFN-B and GFP occurred (B of FIG. 3). In other words, the cleavage of the foreign protein occurred due to the insertion of the furin cleavage site, and the ratio of IFN-B and GFP in the free form was increased.

Example 2

Mammalian cells MDCK, A549, NHBE and Raw 264.7 cells were infected with A/PR8/1934/H1N1 wild-type virus and ΔNS1-86 mIFN-β/GFP virus prepared as in Preparation Example 1, and then proliferation was compared. After infecting each cell with the ΔNS1-86 mIFN-β/GFP virus prepared as in Preparation Example 1 at an MOI of 0.0001, the supernatant was collected 12, 24, 48, and 72 hours later, and MDCK cells were infected with the supernatant. The proliferation of the virus according to each cell was identified. As a result, as shown in FIG. 4, it can be seen that the virus according to the present disclosure was attenuated compared to the wild-type virus.

BALB/c mice were intranasally infected once with A/PR8/1934/H1N1 wild-type virus and ΔNS1-86 mIFN-β/GFP virus prepared as in Preparation Example 1 at a titer of $1 \times 10^{3.5}$ $TCID_{50}/30$ μl, and then changes in body weight, survival rate, and virus titer in lungs of mice were measured for 2 weeks. As a result, as shown in FIG. 5, in the group of mice infected with the A/PR8/1934/H1N1 wild-type virus, all died until the 8th day after infection, but the group of mice infected with the ΔNS1-86 mIFN-β/GFP virus, 100% of them were survived. In other words, it can be seen that the ΔNS1-86 mIFN-β/GFP virus was significantly attenuated compared to the wild-type virus also in infection in mice as in the result of FIG. 4. (p<0.05)

Table 1 shows a measurement of the titers and 50% mouse lethal dose of wild-type A/PR8/1934/H1N1 virus and ΔNS1-

86 mIFN-β/GFP virus in MDCK cells. It can be seen that the ΔNS1-86 mIFN-β/GFP virus was attenuated compared to the wild-type virus even at the virus titer and 50% mouse lethal dose.

[Table 1]

Experimental Infection of Mice with ΔNS1-86 Viruses and PR8/WT Virus

TABLE 1

ΔNS1-86 viruses exhibit different levels of attenuation in vitro and in vivo

| Virus | [a]Viral titer ($\log_{10}$ TCID/ml ± SEM) | Virulence | |
|---|---|---|---|
| | | [b]$MLD_{50}$ ($\log_{10}$TCID/ml) | [c]% Weight loss ± SEM |
| ΔNS1-96 mIFN-β | 5.1 ± 0.23 | >3.0 | 5.6 ± 3.2 |
| ΔNS1-96 GFP | 6.8 ± 0.16 | >5.0 | 4.2 ± 5.3 |
| PR8/WT | 8.6 ± 0.15 | 2.3 | >25.0 |

*$TCID_{50}$ assay for ΔNS1-86 viruses and PR8/WT virus grown in MDCK cells.
[b]50% mouse lethal dose ($MLD_{50}$) for Δ NS1-86 viruses and PR8/WT virus.

Groups of live mice per dose were inoculated intranasally with tenfold serial dilutions containing $10^{2.0}$ to $10^{6.0}$ $TCID_{50}/ml$. Mice that lost 25% body weight were assumed to be near death and were euthanized.
Survival of mice was monitored for 14 days after inoculation
[c]5-week-old female BALB/c mice were inoculated intranasally with $10^{5.0}TCID_{50}/ml$ of the ΔNS1-86 viruses and PR8/WT virus.
Body weight of inoculated mice (n = 10/group) was recorded daily and is given as a percentage of the animal's weight on the day of inoculation.
SEM, standard error of the mean.

Example 3

Figure 6:
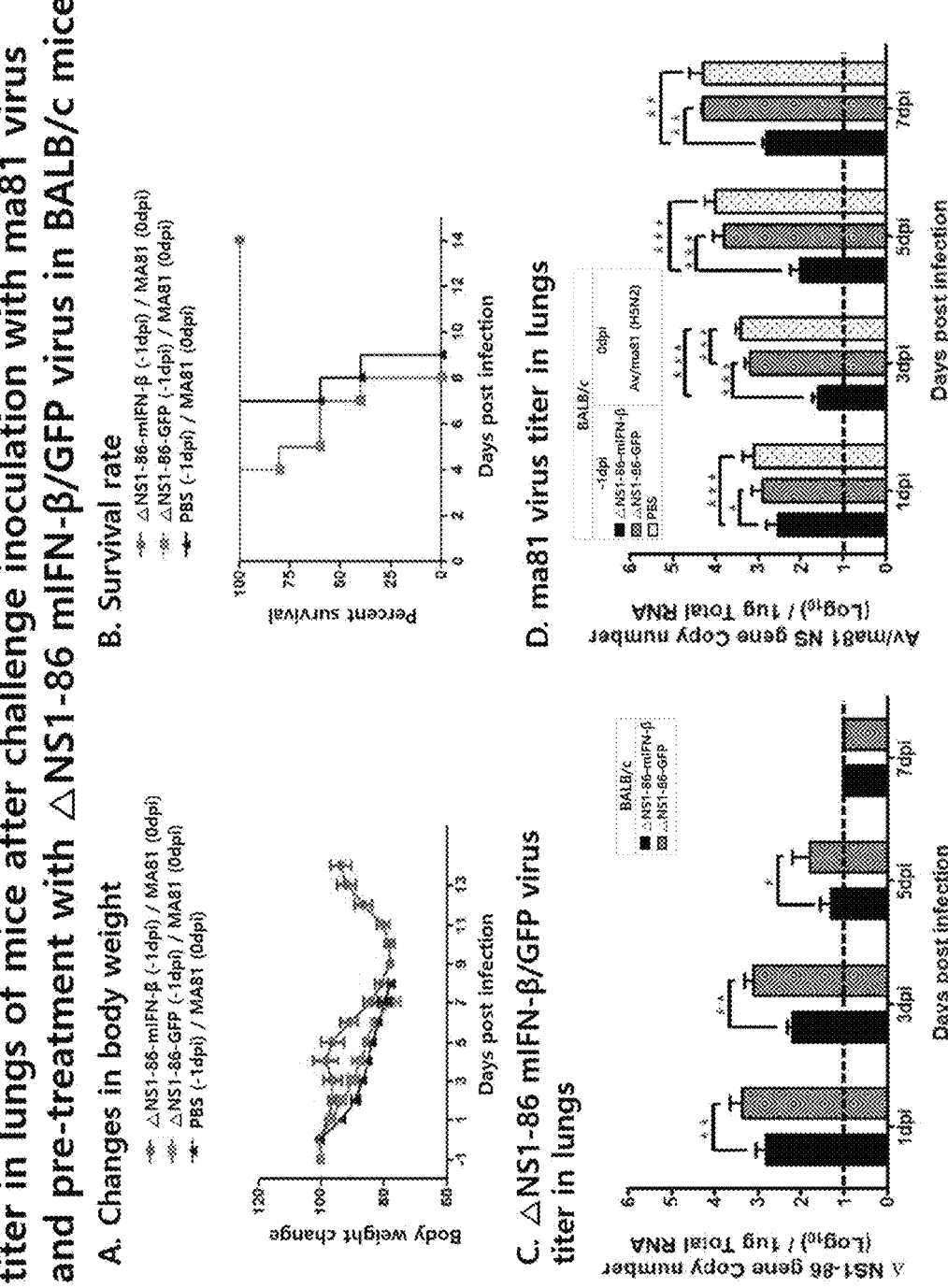
FIG. 6 is a graph illustrating changes in body weight, survival rate, and viral titer in lungs of mice upon challenge inoculation with ma81 virus after pre-treatment with ΔNS1-86 mIFN-β/GFP virus in BALB/c mice.

BALB/c mice were pre-treated with ΔNS1-86 mIFN-β/GFP virus prepared as in Preparation Example 1 and PBS one day before challenge inoculation, and then after challenge inoculation with av/ma81/H5N2 virus, changes in body weight, survival rate, and virus titer in lungs of mice were identified for 2 weeks. As can be seen in FIG. 6, in the group of mice pre-treated with the ΔNS1-86 GFP virus and PBS, all died until the 8th and 10th days after infection, but in the group of mice pre-treated with the NS1-86 mIFN-τ3 virus, weight loss was recovered and 100% of them were survived. (p<0.05)

FIG. 7 is a graph showing the changes in body weight, survival rate, and virus titer in lungs of mice for 2 weeks after B6-Mx+/+ mice carrying the MX1 gene, an interferon response inducing gene, were pre-treated with the ΔNS1-86 mIFN-β/GFP virus prepared as in Preparation Example 1 and PBS one day before challenge inoculation, followed by the challenge inoculation with av/ma81/H5N2 virus. It can be seen that in the group of mice pre-treated with the ΔNS1-86 GFP virus and PBS, all died until the 5th day after infection, but in the group of mice pre-treated with the NS1-86 mIFN-β virus, weight loss was recovered from the 4th day after infection and 100% of them were survived. It can be seen that the titer of the av/ma81 virus in the mouse lungs also decreased, indicating that the av/ma81 virus did not proliferate in the mouse lungs from the 5th day after infection. (p<0.05)

FIG. 8 is a graph showing the changes in body weight, survival rate, and virus titer in lungs of mice for 2 weeks after B6-Mx+/+ mice were post-treated with the ΔNS1-86 mIFN-β/GFP virus prepared as in Preparation Example 1 and PBS one day after challenge inoculation with av/ma81/H5N2 virus. It can be seen that in the group of mice post-treated with the ΔNS1-86 GFP virus and PBS, all died until the 5th day after infection, but in the group of mice post-treated with the NS1-86 mIFN-β virus, weight loss was recovered from the 4th day after infection and 100% of them were survived. It can be seen that the titer of the av/ma81 virus in the mouse lungs also decreased, indicating that the av/ma81 virus did not proliferate in the mouse lungs from the 6th day after infection. (p<0.05)

FIG. 9 shows the results of measuring the expression level of interferon-beta in the bal-fluid of all mouse groups infected and treated with ΔNS1-86 mIFN-β/GFP virus and A/PR8/1934/H1N1 wild-type virus from FIGS. 4 to 7. It can be seen that there was a significantly higher interferon-beta expression level in the bal-fluid of the mouse groups pre-/post-treated with the ΔNS1-86 mIFN-β virus compared to the mouse groups treated with ΔNS1-86 GFP virus and A/PR8/1934/H1N1 wild-type virus. (p<0.05)

FIG. 10 is a graph showing the changes in body weight, survival rate, and virus titer in lungs of mice for 2 weeks after hDPP4 mice were post-treated with the ΔNS1-86 mIFN-β/GFP virus prepared as in Preparation Example 1 and PBS one day after challenge inoculation with MERS-CoV virus. It can be seen that in the group of mice post-treated with PBS, all mice died until the 11th day after infection, but in the group of mice post-treated with the ΔNS1-86 mIFN-β virus, weight loss was recovered from the 8th day after infection and 100% of them were survived. It can be seen that the titer of the MERS-CoV virus in the mouse lungs also decreased, indicating that the MERS-CoV virus did not proliferate in the mouse lungs from the 8th day after infection. (p<0.05)

Hereinbefore, the present disclosure has been described with reference to the preferred embodiments. It will be understood by those skilled in the art that the present disclosure may be embodied in various other forms without departing from the essential characteristics thereof. Therefore, the disclosed embodiments should be considered in an illustrative rather than a restrictive perspective. The scope of the present disclosure is defined by the appended claims rather than by the preceding description, and all differences within the scope of equivalents thereof should be construed as being included in the present disclosure.

---

The invention claimed is:

1. A recombinant influenza virus comprising a nucleic acid encoding a truncated NS1 protein of SEQ ID NO: 12.

2. A genetic vector comprising a nucleic acid encoding a truncated NS1 protein of SEQ ID NO: 12.

3. A vaccine composition for preventing or treating influenza virus or MERS-COV virus comprising the recombinant influenza virus of claim 1 as an active ingredient.

4. The vaccine composition of claim 3, wherein the vaccine is a live vaccine in which the virus has been attenuated.

5. The vaccine composition of claim 3, wherein the vaccine induces an immune response against subtype A/Ab/Korea/ma81/07/H5N2 (Av/ma81) mammalian adaptive avian influenza virus and MERS-COV virus.

6. A method for preventing or treating influenza virus or MERS-COV virus infection by administering an effective amount of the vaccine of claim 3 to a subject.

* * * * *